(12) United States Patent
Schmand et al.

(10) Patent No.: US 9,194,959 B2
(45) Date of Patent: Nov. 24, 2015

(54) POSITRON EMISSION TOMOGRAPHY DETECTOR BASED ON MONOLITHIC SCINTILLATOR CRYSTAL

(75) Inventors: Matthias J. Schmand, Lenoir City, TN (US); Debora Henseler, Erlangen (DE)

(73) Assignees: Siemens Medical Solutions USA, Inc., Malvern, PA (US); Siemens Aktiengesellschaft, Munich (DE)

( * ) Notice: Subject to any disclaimer, the term of this patent is extended or adjusted under 35 U.S.C. 154(b) by 526 days.

(21) Appl. No.: 13/540,674

(22) Filed: Jul. 3, 2012

(65) Prior Publication Data

US 2013/0009067 A1 Jan. 10, 2013

Related U.S. Application Data

(60) Provisional application No. 61/504,820, filed on Jul. 6, 2011.

(51) Int. Cl.
*G01T 1/164* (2006.01)
*A61B 6/03* (2006.01)
*G01T 1/29* (2006.01)

(52) U.S. Cl.
CPC ............ *G01T 1/1642* (2013.01); *A61B 6/037* (2013.01); *G01T 1/1644* (2013.01); *G01T 1/2985* (2013.01)

(58) Field of Classification Search
CPC ..... G01T 1/2985; G01T 1/1644; A61B 6/037
USPC .................................................. 250/363.03
See application file for complete search history.

(56) References Cited

U.S. PATENT DOCUMENTS

| 2004/0227091 | A1* | 11/2004 | LeBlanc et al. | 250/366 |
| 2004/0262526 | A1* | 12/2004 | Corbeil et al. | 250/367 |
| 2009/0008562 | A1* | 1/2009 | Grazioso et al. | 250/363.04 |
| 2009/0032717 | A1* | 2/2009 | Aykac et al. | 250/367 |
| 2010/0108893 | A1* | 5/2010 | Flitsch et al. | 250/361 R |
| 2013/0056638 | A1* | 3/2013 | Inadama et al. | 250/362 |

FOREIGN PATENT DOCUMENTS

WO WO 2011121707 A1 * 6/2011

* cited by examiner

*Primary Examiner* — Christine Sung
(74) *Attorney, Agent, or Firm* — Peter Kendall

(57) ABSTRACT

A high-resolution nuclear imaging detector for use in systems such as positron emission tomography includes a monolithic scintillator crystal block in combination with a single photomultiplier tube read-out channel for timing and total energy signals, and one or more solid-state photosensor pixels arrays on one or more vertical surfaces of the scintillator block to determine event position information.

28 Claims, 3 Drawing Sheets

POSITRON EMISSION TOMOGRAPHY DETECTOR BASED ON MONOLITHIC SCINTILLATOR CRYSTAL

CROSS-REFERENCE TO RELATED APPLICATIONS

This application claims the benefit of U.S. Provisional Patent Application 61/504,820, filed on Jul. 6, 2011, the entire disclosure of which is hereby incorporated by reference.

TECHNICAL FIELD

The current invention relates to the field of nuclear medical imaging systems. Particularly, the invention relates to providing a high-resolution Positron Emission Tomography (PET) detector by using a monolithic scintillator crystal block.

BACKGROUND OF THE INVENTION

Medical imaging is one of the most useful diagnostic tools available in modern medicine. Medical imaging allows medical personnel to non-intrusively look into a living body in order to detect and assess many types of injuries, diseases, conditions, etc. Medical imaging allows doctors and technicians to more easily and correctly make a diagnosis, decide on a treatment, prescribe medication, perform surgery or other treatments, etc.

There are medical imaging processes of many types and for many different purposes, situations, or uses. They commonly share the ability to create an image of a bodily region of a patient, and can do so non-invasively. Examples of some common medical imaging types are nuclear medical (NM) imaging such as positron emission tomography (PET) and single photon emission computed tomography (SPECT), electron-beam X-ray computed tomography (CT), magnetic resonance imaging (MRI), and ultrasound (US). Using these or other imaging types and associated machines, an image or series of images may be captured. Other devices may then be used to process the image in some fashion. Finally, a doctor or technician may read the image in order to provide a diagnosis.

In positron emission tomography (PET), the detector needs to have a high efficiency (energy range of 511 keV), and it needs to detect this radiation with sufficient energy resolution (10-15% FWHM) to distinguish unscattered from scattered and background radiation. The detector also needs to count single events and provide a very accurate timing resolution of few ns or better, in order to identify coincidences between pairs of 511 keV events that originate from the same positron decay. In addition, a spatial resolution of a few mm is required for clinical systems and in the <1 mm range for pre-clinical applications.

State-of-the-art PET detectors are mostly based on scintillators and photosensors. The scintillator converts the high-energy gamma radiation into visible light, then the photodetector converts the visible photons into an electrical signal, which is usually further amplified by the front-end readout electronics.

The standard detector design today is a block detector, in which an array of discrete scintillator crystals is viewed by a smaller number of photomultiplier tubes (PMTs). This optical multiplexing leads to a strong reduction of the number of sensor channels and electronics channels, compared to the number of scintillator crystals. The event position then can be obtained by calculating the centroid of the detected PMT signals and assigning the event to one of the discrete crystals by a lookup map.

Another approach uses a large continuous scintillator crystal with an array of PMTs, where the event positions are determined by classic Anger centroid calculation from the PMT signals, similar to a SPECT detector. NaI(Tl) scintillator plates are mostly used for such designs. The drawback of this approach is that the positioning becomes less accurate at areas of high crystal thickness, especially near the edges of the scintillator plate. In the case of NaI(Tl), the timing resolution is relatively poor due to the long decay time, and the pile-up of simultaneous events on the scintillator plate becomes problematic at higher count rates.

The present invention provides a high-resolution PET detector, which simultaneously provides good energy resolution, good timing and accurate position information up to the scintillator edges.

SUMMARY OF THE INVENTION

In accordance with an embodiment of the invention, a positron emission tomography (PET) detector includes a monolithic scintillator crystal block in combination with a single photomultiplier tube read-out channel for timing and total energy and one or more arrays of solid-state photosensor pixels to determine event position information.

Further provided is a plurality of configurations with the solid-state photosensor pixel arrays on up to four vertical surfaces of the scintillator block, or five total surfaces. This aids in reducing the edge effects that usually deteriorate the resolution significantly when only one face is used for the position read-out.

Further provided are different structures for the monolithic scintillator. Specifically, using a combination of monolithic crystals and pixelated crystals to keep photons generated near the edges of the detector from spreading to the rest of the crystal.

BRIEF DESCRIPTION OF THE DRAWINGS

In order to describe the manner in which the features of the present disclosure can be obtained, a more particular description of the principles briefly described above will be rendered by reference to specific examples thereof which are illustrated in the appended drawings. Understanding that these drawings depict only example embodiments of the disclosure and are not therefore to be considered to be limiting of its scope, the principles herein are described and explained with additional specificity and detail through the use of the accompanying drawings in which.

DETAILED DESCRIPTION OF THE INVENTION

As required, disclosures herein provide detailed embodiments of the present invention; however, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention.

Figure 1:
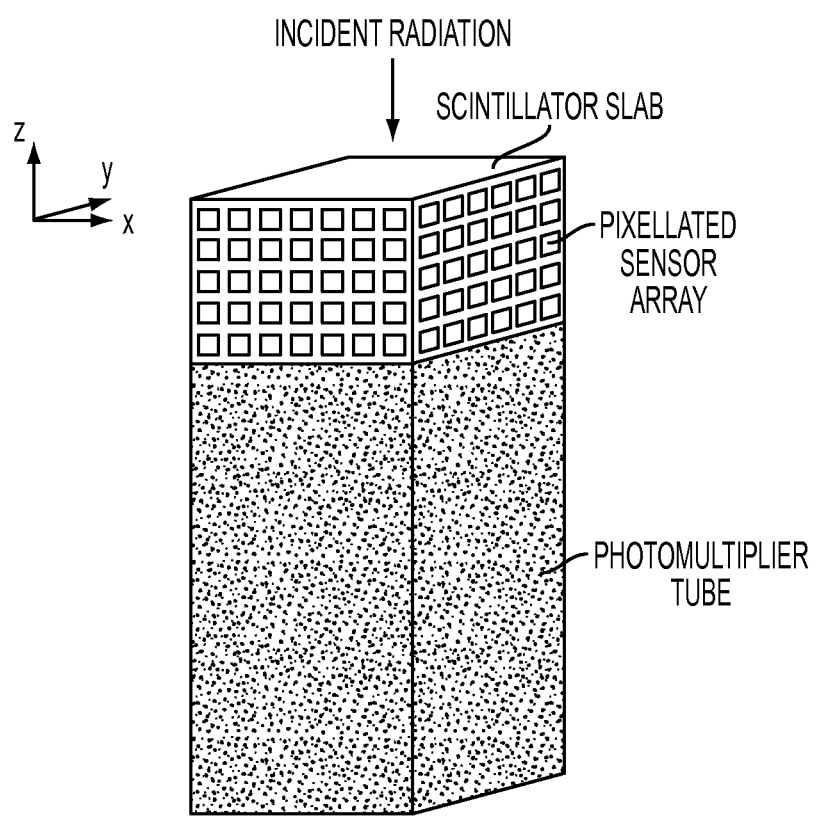
FIG. 1 shows a PET detector block, based on a monolithic scintillator crystal, a PMT on the face of the crystal opposite the incident radiation, and several two-dimensional arrays of solid-state sensor pixels, in accordance with an example implementation of the present technology.

FIG. 1 shows a PET detector block in accordance with one embodiment of the invention. The detector includes a monolithic scintillator crystal block or scintillator slab, a photomultiplier tube (PMT), and one or more arrays of pixelated solid-state photosensors. The scintillator face opposite the incident radiation is coupled to the PMT, either directly or via an additional light guide that is not shown in the drawing. The PMT can have a square, rectangular or rounded entrance window. The size of the entrance window should be matched to the size of the scintillator face and the interface area should be maximized. The purpose of this PMT is to collect a large portion of the emitted visible photons, many of them directly from where they are emitted at the face of the scintillator crystal block. The signal from this PMT is then used to provide the energy and timing information for each event with high accuracy. The timing information and total energy can be obtained from a single PMT channel with high signal-to-noise ratio. The photons detected by the PMT will have a large fraction of direct emission pathways, improving the timing resolution by lowering the time spread due to differences in path length. The resulting PMT signal has a very large gain, a short pulse shape and low noise, which is very well suited to providing high energy and timing resolution. Only one channel is needed for this, and conventional PMT read-out electronics with a high maturity can be used for the signal shaping and pulse discrimination, since the available space for this one channel is not too confined. Integrated or hybrid signal processing can be used for the amplification, shaping, pole-zero compensation and pulse discrimination for timing.

Due to the large lateral dimensions of the scintillator block, the favorable aspect ratio, and the absence of an internal crystal interface, the detector will have a large overall light output, as compared to pixel-based block detectors. An advantage of this design is that the aspect ratio of the large scintillator crystals is very favorable. The coupling interface is large, and therefore a large fraction of the photons can reach the PMT directly, without being absorbed, scattered or reflected at interfaces. This will also lead to short optical path length differences and low time spreads over the photon distribution. The typical light losses at crystal-to-crystal, crystal-to-air or crystal-to-reflector interfaces of pixelated block detectors are also avoided.

In addition to the single-PMT read-out channel, there are arrays of solid-state photosensors on one or more sides of the scintillator block. These photosensors can for example be silicon photomultipliers (SiPMs), avalanche photodiodes (APDs), p-i-n photodiodes or any other type of solid-state or semiconductor sensor, operated in counting mode. They can be either monolithic arrays or can be assembled from discrete sensor pixels. The purpose of these sensor arrays is to provide the position information for each event by an Anger weighting of the signals for the various pixels. If these are two-dimensional arrays (as pictured in FIG. 1) they will provide position data for the x, y and z coordinates, It is also possible to use one-dimensional arrays to provide x and y information only, without the depth-of-interaction (i.e. z-coordinate) information.

The position information obtained from the sensor arrays can further be used to correct the energy and timing output from the PMT channel, based on a position-dependent lookup table in x,y or x,y,z.

Figure 2:
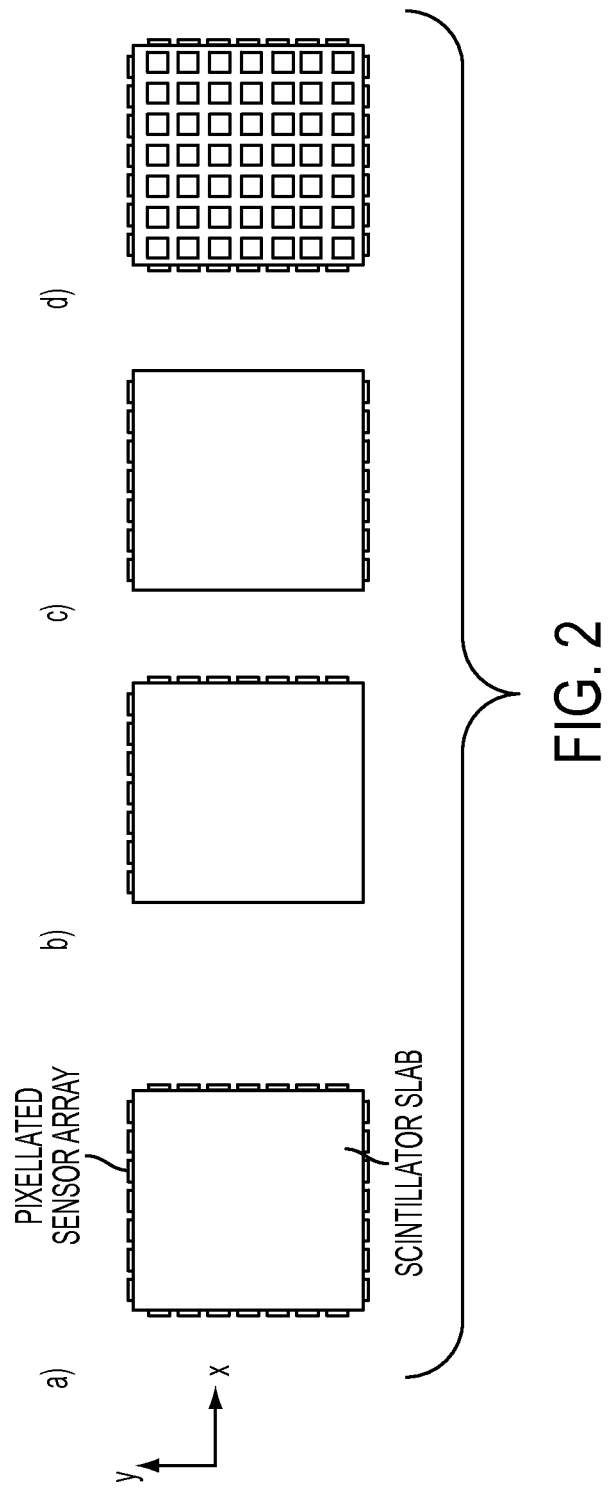
FIG. 2 shows four different sample configurations with different numbers of sensor arrays covering different sides of the scintillator block, in accordance with another example implementation of the present technology.

FIG. 2 shows a plurality of different sample solid-state sensor configurations with sensors on up to four of the vertical surfaces or five total surfaces. By using the position information from several surfaces, it is possible to reduce the edge effects that usually deteriorate the resolution significantly when only one face is used for the position read-out. In particular, FIG. 2a shows pixelated sensor arrays on all four vertical surfaces of the scintillator slab; FIG. 2b shows sensor arrays on two adjacent vertical surfaces; FIG. 2c show sensor arrays on two opposite vertical surfaces. In addition to one or more of the vertical surfaces, the surface that faces the incident radiation also can be covered by such a sensor array, as shown in FIG. 2d. In this example, the incoming 511 keV gamma photons would be only slightly attenuated by the solid-state sensor, but would not be absorbed by the sensor. The attenuation of 511 keV radiation in thin silicon sensors, such as SiPMs and APDs, is usually negligible. If the top side is also read out, this additional information will further contribute to the accuracy of the positioning information, especially near the scintillator edges and corners and for scintillation events interacting close to the incident surface.

Any surfaces that are not covered by sensor arrays can be coated with a reflector material, in order to increase the light output at the PMT and at those sides covered by read-out solid-state sensor arrays. Similarly, it is possible to coat any gaps between the sensor pixel areas with a reflective material.

The sensor pixels can be evenly spaced, as shown in FIG. 2, or alternatively can be non-uniformly spaced, e.g. increasing in density towards the edges and corners, in order to even further minimize the edge effects. The pixel shape can also differ from the perfect square shape shown in FIG. 2. Examples of other pixel shapes would be rectangular, hexagonal, triangular or round pixel shapes.

A number of advantages arise from the special case where SiPM arrays are used to read out the positioning signals. SiPM devices are well suited for reading out PET signals, because they have a high internal gain (similar to PMT gains), relatively high quantum efficiency, and can be read out with low noise. Like other solid-state photosensors, they have the advantage of a compact size and the possibility for high integration density. Compared to APDs, the temperature sensitivity is somewhat lower, and there is less need for elaborate pre-amplification and signal shaping electronics, because the signals coming out of the SiPM devices are already quite large. SiPM signals are very fast, thus allowing a relatively high event rate before pile-up of the signals occurs. However, SiPMs have an intrinsic signal non-linearity due to the limited number of Geiger-mode avalanche cells. This non-linearity will be relatively small if the signal is spread over a large number of devices. Additionally, it is always possible to correct for such non-linearity effects by post-processing of the signals.

SiPMs also have the advantage that they can be manufactured in Complementary Metal-Oxide-Semiconductor (CMOS) compatible processes. Additional features such as amplifiers, shapers or analog-to-digital converters (ADCs) can already be integrated on the sensor substrate. With a CMOS device, it is even possible to address all the sub-cells of the SiPM device separately and therefore drastically increase the possible position resolution. In another possible embodiment, CMOS processing could even be used to output Anger-weighted 2D position information, directly, for each of the various sensor arrays. A post-processing algorithm could then be used to determine the most probable overall (x,y,z) position from the various array outputs.

If the signals of all sensor pixels are used for the position calculation, the requirements for the signal-to-noise ratios may be difficult to achieve, as the noise from a large number of pixels will add up and eventually degrade the quality of the position information if too large. If the noise per pixel is too high (e.g. due to dark noise or electronics noise), it is possible to select only a subset of the sensor pixels for use in the positioning algorithm. For example, only those pixels having output signals crossing a certain signal threshold could be included, or only a certain predetermined number of signals ordered by decreasing signal height could be included in the position calculation algorithm. This could significantly reduce the blurring of the position profile due to various noise components. The read-out of the sensor pixels could be triggered either by one of these sensors crossing a certain threshold or by the PMT signal crossing the lower threshold of the energy window.

Figure 3:
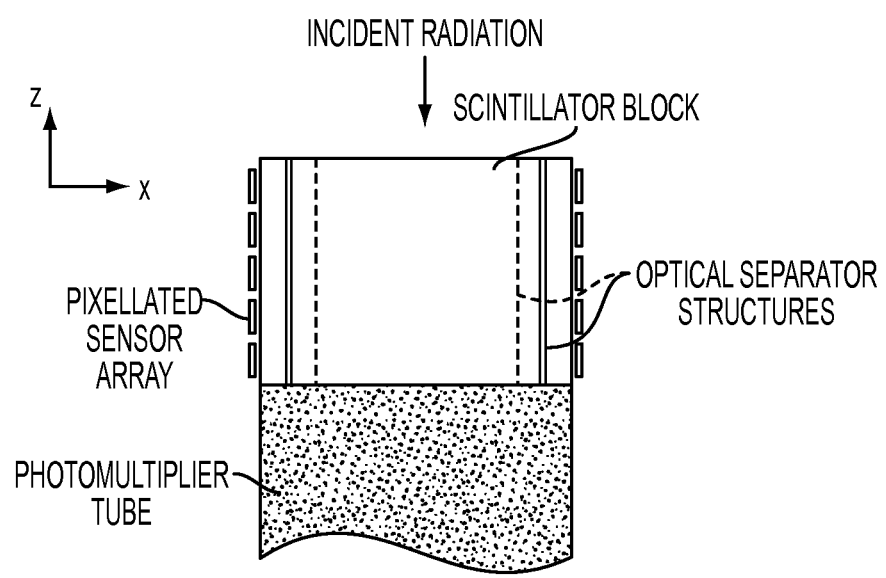
FIG. 3 shows a schematic view of the xz cross section of a monolithic scintillator detector with optical separator structures, in accordance with an example implementation of the present technology.

FIG. 3 shows a structured monolithic scintillator crystal. The center part of the scintillator is unstructured and transparent. The edges along the x and y spatial directions are optically separated or isolated from the center part of the crystal by an optical separating or boundary structure. In this embodiment, each edge region is split into two different zones with different degrees of optical separation (e.g. by a different density of scatter centers or a different scatter probability at each scatter element). Optical boundaries can be created within the crystal using any number of known techniques including creation of voids along a plane using a laser. The advantage of such an optical structuring is that the photons generated near the edges do not spread into the rest of the crystal, and the positioning near the edges therefore becomes more accurate. The advantages of a monolithic crystal (for the center areas) and a pixelated crystal (for the edge resolution) are combined. In another possible embodiment, the optical separator structures may only extend over part of the scintillator height in the z direction.

A monolithic block detector according to the present invention has the potential for a high detection efficiency at 511 keV. Those events that undergo Compton scattering at the first interaction site still have a considerable probability of interacting again within the same scintillator block and depositing a sum energy of 511 keV in this crystal. The signal on the PMT will be proportional to the total deposited energy, while the position is determined from the combined sensor arrays. If the granularity of the sensors is coarse, this will yield an average position somewhere between the first and second interaction sites. A fine granularity however, further opens up the possibility to identify both interaction sites and to select the first interaction position for generating the line of response for the positron decay. A high integration of the sensor array with a first part of the read-out and signal processing electronics would certainly help with such correction procedures.

The invention having been thus described, it will be apparent to those skilled in the art that the same may be varied in many ways without departing from the spirit of the invention. Any and such modifications are intended to be covered within the scope of the following claims. For example, while the invention has been described with respect to a PET detector, the novel gamma radiation detector could be used for other applications, such as SPECT, depth-of-interaction imaging, Compton scatter imaging, etc.

What is claimed is:

1. A high-resolution nuclear radiation imaging detector, comprising:
    a monolithic scintillator crystal block;
    a photomultiplier tube optically coupled to a surface of the monolithic scintillator crystal block normal to incident radiation; and
    at least one solid-state photosensor pixel array optically coupled to at least one surface of the monolithic scintillator crystal block other than a surface normal to incident radiation.

2. A high-resolution nuclear radiation imaging detector as set forth in claim 1, wherein said monolithic scintillator crystal block is structured into separate optical zones.

3. A high-resolution nuclear radiation imaging detector as set forth in claim 2, wherein said monolithic scintillator crystal block is separated into a center section and edge sections.

4. A high-resolution nuclear radiation imaging detector as set forth in claim 3, wherein said center section is unstructured and transparent.

5. A high-resolution nuclear radiation imaging detector as set forth in claim 3, wherein said edge sections are split into two different zones with different degrees of optical separation.

6. A high-resolution nuclear radiation imaging detector as set forth in claim 5, wherein said different degrees of optical separation are provided by a different density of scatter centers.

7. A high-resolution nuclear radiation imaging detector as set forth in claim 5, wherein said different degrees of optical separation are provided by a different scatter probability at each scatter element.

8. A high-resolution nuclear radiation imaging detector as set forth in claim 1, wherein said photomultiplier tube has a single channel.

9. A high-resolution nuclear radiation imaging detector as set forth in claim 1, wherein said photomultiplier tube has a square entrance window.

10. A high-resolution nuclear radiation imaging detector as set forth in claim 1, wherein said photomultiplier tube has a rectangular entrance window.

11. A high-resolution nuclear radiation imaging detector as set forth in claim 10, wherein said entrance window is matched in size with a scintillator face of said monolithic scintillator crystal.

12. A high-resolution nuclear radiation imaging detector as set forth in claim 1, wherein said photomultiplier tube has a rounded entrance window.

13. A high-resolution nuclear radiation imaging detector as set forth in claim 1, wherein said solid-state photosensor pixel arrays are silicon photomultipliers.

14. A high-resolution nuclear radiation imaging detector as set forth in claim 1, wherein said solid-state photosensor pixel arrays are avalanche photodiodes.

15. A high-resolution nuclear radiation imaging detector as set forth in claim 1, wherein said solid-state photosensor pixel array are p-i-n photodiodes.

16. A high-resolution nuclear radiation imaging detector as set forth in claim 1, wherein said solid-state photosensor pixel array is one-dimensional.

17. A high-resolution nuclear radiation imaging detector as set forth in claim 1, wherein said solid-state photosensor pixel array is two-dimensional.

18. A high-resolution nuclear radiation imaging detector as set forth in claim 1, further comprising a second solid-state photosensor pixel array provided on a second surface of the scintillator block.

19. A high-resolution nuclear radiation imaging detector as set forth in claim 18, wherein said second surface is adjacent to said at least one surface.

20. A high-resolution nuclear radiation imaging detector as set forth in claim 18, wherein said second surface is opposite to said at least one surface.

21. A high-resolution nuclear radiation imaging detector as set forth in claim 18, further comprising a third solid-state photosensor pixel array provided on a third surface of the scintillator block.

22. A high-resolution nuclear radiation imaging detector as set forth in claim 21, further comprising a fourth solid-state photosensor pixel array provided on a fourth surface of the scintillator block.

23. A high-resolution nuclear radiation imaging detector as set forth in claim 1, further comprising a solid-state photosensor pixel array provided on a surface of the scintillator block incident to gamma event radiation.

24. A high-resolution nuclear radiation imaging detector as set forth in claim 1, wherein an area of the scintillator block that is not covered by a photosensor pixel array is covered with a reflective material.

25. A high-resolution nuclear radiation imaging detector as set forth in claim 1, where photosensor pixels are spaced uniformly.

26. A high-resolution nuclear radiation imaging detector comprising:
   a monolithic scintillator crystal block;
   a photomultiplier tube optically coupled to one surface of the monolithic scintillator crystal block; and
   at least one solid-state photosensor pixel array optically coupled to another surface of the monolithic scintillator crystal block, where photosensor pixels are spaced non-uniformly.

27. A PET imaging system, comprising a high-resolution nuclear radiation imaging detector as set forth in claim 1.

28. A PET imaging system, comprising a high-resolution nuclear radiation imaging detector as set forth in claim 26.

* * * * *